United States Patent

Schacht et al.

[11] 4,053,626
[45] Oct. 11, 1977

[54] CHOLESTEROL LEVEL-LOWERING PHENOXYACETIC ACIDS

[75] Inventors: Erich Schacht; Werner Mehrhof; Herbert Nowak; Zdenek Simane; Detlev Kayser, all of Darmstadt, Germany

[73] Assignee: Merck Patent Gesellschaft mit beschraenkter Haftung, Darmstadt, Germany

[21] Appl. No.: 724,232

[22] Filed: Sept. 17, 1976

Related U.S. Application Data

[62] Division of Ser. No. 449,332, March 8, 1974, Pat. No. 3,992,386.

[30] Foreign Application Priority Data

Mar. 13, 1973 Germany .............................. 2312344
Apr. 18, 1973 Germany .............................. 2319642
May 18, 1973 Germany .............................. 2325184

[51] Int. Cl.$^2$ ............... C07D 311/04; A61K 31/38
[52] U.S. Cl. ........................... 424/275; 424/283; 260/327 TH; 260/345.2
[58] Field of Search ............... 260/327 TH, 345.2; 424/275, 283

[56] References Cited

U.S. PATENT DOCUMENTS 3,471,520  10/1969  Irmscher et al. .................. 260/345.2
3,535,344  10/1970  Irmscher et al. .................. 260/345.2

Primary Examiner—Cecilia M. S. Jaisle
Attorney, Agent, or Firm—Millen & White

[57] ABSTRACT

Phenoxyacetic acids of the formula

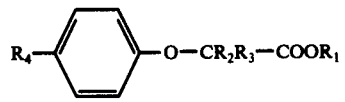

wherein $R_1$ is H or alkyl of 1–4 carbon atoms; $R_2$ is H, or when $R_4$ is Q, also alkyl of 1–4 carbon atoms; $R_3$ is methyl, phenyl or chlorophenyl; and $R_4$ is piperidino, isoindolino, 1,2,3,4-tetrahydroquinolino, 1-$R_5$-1,2,3,4-tetrahydro-4-quinolyl, 4-piperidinophenyl, 4-piperidinophenoxy, 1-pyrryl, or Q, wherein $R_5$ is H or alkyl of 1–4 carbon atoms; and Q is 4-oxo-1,2,3,4-tetrahydroquinolino, 4-hydroxy-1,2,3,4-tetrahydroquinolino, 4-chromanyl, 4-thiochromanyl or 1-phenyl-1,2,3,4-tetrahydro-4-quinolyl; and the salts thereof, possess cholesterol level-lowering activity.

8 Claims, No Drawings

CHOLESTEROL LEVEL-LOWERING PHENOXYACETIC ACIDS

This is a division of application Ser. No. 449,332, filed Mar. 8, 1974, now U.S. Pat. No. 3,992,386, patented Nov. 16, 1976.

BACKGROUND OF THE INVENTION

This invention relates to novel phenoxyacetic acid derivatives.

SUMMARY OF THE INVENTION

The novel compounds of this invention are phenoxyacetic acid derivatives of the Formula I

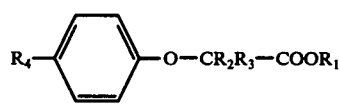

wherein $R_1$ and $R_5$ each are H or alkyl of 1–4 carbon atoms; $R_2$ is H, or when $R_4$ is Q, H or alkyl of 1–4 carbon atoms; $R_3$ is methyl, phenyl or chlorophenyl; and $R_4$ is piperidino, isoindolino, 1,2,3,4-tetrahydroquinolino, 1-$R_5$-1,2,3,4-tetrahydro-4-quinolyl, 4-piperidinophenyl, 4-piperidinophenoxy, 1-pyrryl, or Q, wherein $R_5$ is H or alkyl of 1–4 carbon atoms and Q is 4-oxo-1,2,3,4-tetrahydroquinolino, 4-hydroxy-1,2,3,4-tetrahydroquinolino, 4-chromanyl, 4-thiochromanyl or 1-phenyl-1,2,3,4-tetrahydro-4-quinolyl, and the physiologically acceptable salts thereof with acids or bases.

DETAILED DISCUSSION

The class of compounds of Formula I comprise compounds of Formulae Ia through Ig (wherein $R_1$, $R_2$ and $R_3$ have the values given above):

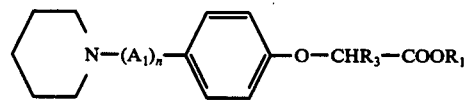

($A_1$ is p-$C_6H_4$— or p-$C_6H_4$—O—; n is 0 or 1)

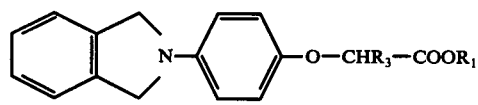

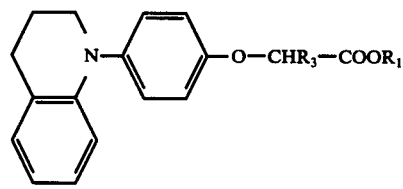

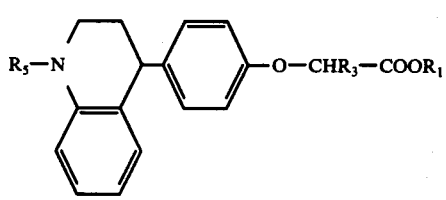

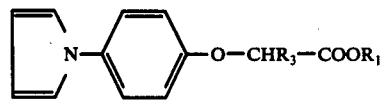

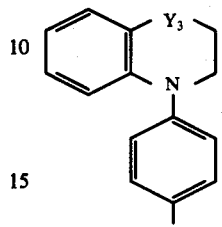

($Y_3$ is —CO— or —CHOH—)

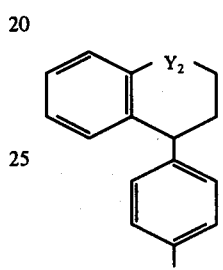

($Y_2$ is O, S or N—$C_6H_5$)

More particularly, compounds of Formulae I and Ia through Ig include those wherein Ih. $R_1$ is H, $CH_3$ or $C_2H_5$;
Ii. $R_2$ is H or $CH_3$, especially those of Ih;
Ij. $R_3$ is $CH_3$, $C_6H_5$, m-chlorophenyl or p-chlorophenyl, preferably $C_6H_5$ or p-chlorophenyl, especially those of Ih and Ii.

Compounds of Formulae Ic, Id, If and Ig, particularly those defined in Ih, Ii and Ij above, are especially valuable from a pharmaceutical viewpoint.

In its process aspect, this invention relates to a process for the production of compounds of Formula I, as well as the physiologically acceptable salts thereof with acids or bases, wherein:

a. a phenol of general Formula II

wherein $R_4$ has the values given for Formula I, is reacted with a compound of general Formula III $$X—CR_2R_3—COOR_1 \qquad \text{III}$$

wherein X is Cl, Br, I, OH or esterified OH and $R_1$, $R_2$ and $R_3$ each have the values given for Formula I, or is reacted together with a haloform and a carbonyl compound of the general formula $R_2$—CO—$R_3$ (wherein $R_2$ and $R_3$ have the values given for Formula I); or b. a compound of general Formula IV

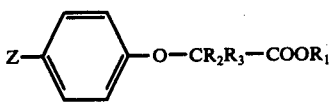

IV wherein Z is $Z_1$—$Y_1$—NH—$(A_1)_n$—, $Z_2$—$CH_2CH_2$—$N(C_6H_5)$—, $C_6H_5$—$Y_2$—$CH_2CH_2$—CHX—, or $HY_2$—(o—$C_6H_4$)—$CH(CH_2CH_2X)$—, Y is pentamethylene or o-xylylene, $Z_1$ is Cl, Br, I, $NH_2$, OH, or an esterified or etherified OH-group, $Z_2$ is a free COOH-group, or a COOH-group present in the form of a functional derivative, $Y_2$ is O, S or $NC_6H_5$, and $R_1$, $R_2$, $R_3$, $A_1$ and $n$ have the values given above, is reacted with a cyclizing agent; or c. in a compound of general Formula V

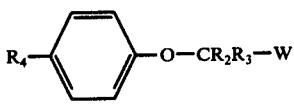

V wherein W is a functionally modified carboxyl group which is different than $COOR_1$, and $R_2$, $R_3$ and $R_4$ have the values given above, the group W is converted into the group $COOR_1$ by treatment with a solvolyzing agent; or d. a compound of general Formula VI $R_4 - X_1$      VI wherein $X_1$ is H, M or X; M is an equivalent of a metallic atom, and $R_4$ and X have the values given above, is reacted with a compound of general Formula VII

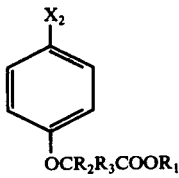

VII wherein $X_2$ is H, Cl, Br, I, $NH_2$ or $SO_3M$, and M, $R_1$, $R_2$ and $R_3$ have the values given above, with the provision that $X_1$ and $X_2$ are not alike and one is H or optionally M; or e. a compound of general Formula VIII

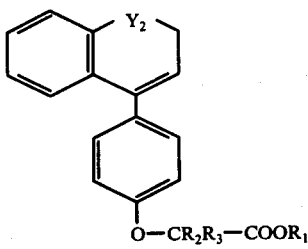

VIII wherein $Y_2$, $R_1$, $R_2$ and $R_3$ have the values given above, is reduced with a reducing agent; or f. a compound of general Formula IX

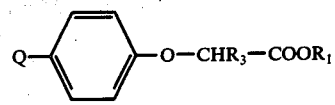

IX wherein $R_1$, $R_3$ and Q have the values given for Formula I, is treated with an alkylating agent; and optionally, in a thus-obtained compound of Formula I, an $R_1$ group is converted into another $R_1$ group by treatment with an esterifying, interesterifying or solvolyzing agent and/or a thus-produced oxo compound is converted into the corresponding hydroxy compound by treatment with a reducing agent or a thus-obtained hydroxy compound is converted into the corresponding oxo compound by treatment with an oxidizing agent and/or a thus-produced compound of Formula I is converted, by treatment with an acid or base, into a physiologically acceptable acid addition or metal or ammonium salt thereof, respectively, and/or a compound of Formula I is liberated from a salt thereof with an acid or a base, by treatment with a base or with an acid, respectively.

In the above formulae, $R_1$ and $R_2$ each preferably are H. When $R_1$ and $R_5$, which can be alike or different, are lower-alkyl, they preferably are methyl or ethyl, but can also be n-propyl, isopropyl, n-butyl, isobutyl, sec.-butyl or tert.-butyl, Hereinbelow, A stands for alkyl of 1 to 4 carbon atoms.

X and $Z_1$ are preferably Cl or Br but can also be, in addition to free OH and I, for example, alkylsulfonyloxy, especially of 1–6 carbon atoms (e.g., methanesulfonyloxy), arylsulfonyloxy, particularly of 6–10 carbon atoms and 1–2 separate or fused rings (e.g., benzenesulfonyloxy, p-toluenesulfonyloxy, 1- or 2-naphthalenesulfonyloxy), or acyloxy, especially alkanoyloxy or 1–7 carbon atoms (e.g., acetoxy) and carbocycloaroyloxy (e.g., benzoyloxy); $Z_1$ can also be $NH_2$ or an etherified OH-group of 1–7 carbon atoms, preferably methoxy or benzyloxy.

The production methods described hereinbelow in greater detail are executed in accordance with the conditions described in the literature for these reactions and suitable therefor.

Preferably, compounds of Formula I are obtained by reacting a phenol II with an acetic acid derivative III. The phenols II are, in part, known. They can be prepared according to methods known per se from the literature, for example by splitting the methyl ethers thereof (compounds otherwise corresponding to those of Formula II, but having an $OCH_3$ in place of OH) with HBr. For the most part, compounds of Formula III are known. They can likewise be produced according to conventional methods.

A phenol II can first be converted into a salt, particularly into a metal salt, e.g., an alkali metal salt, preferably a Li, Na or K salt. For purposes of salt formation, the phenol can be reacted with a reagent forming metal salts (e.g., an alkali metal, such as Na, an alkali metal hydride or amide, such as LiH, NaH, $NaNH_2$ or $KNH_2$), a lower alkali metal alcoholate, such as lithium, sodium or potassium methylate, ethylate or tert.-butylate, an organometallic compound, such as butyllithium, phenyllithium or phenylsodium, a metal hydroxide, carbonate or bicarbonate, such as lithium, sodium, potassium or calcium hydroxide, carbonate or bicarbonate. The salt of II is advantageously produced in the presence of a solvent, e.g., a hydrocarbon, such as hexane, benzene, toluene, or xylene; an ether, such as diethyl ether, diisopropyl ether, tetrahydrofuran (THF), dioxane or diethylene glycol dimethyl ether; an amide, such as dimethylformamide (DMF), or hexamethylphosphoric triamide (HMPA); an alcohol, such as methanol or ethanol; a ketone, such as acetone or butanone; or also a solvent mixture. The phenol II or preferably a salt thereof is reacted with compound III, preferably in the presence of a diluent, e.g., the solvent used for the preparation of the salt, but which can be replaced by another solvent or diluted with such a solvent. The reaction is normally conducted at temperatures of between $-20°$ and $150°$, preferably between $20°$ and $120°$, particularly advantageously at the boiling temperature of the solvent. The reaction can be accomplished under an inert gas, e.g., nitrogen. The phenolate can also be formed in situ, in which case the phenol II and compound III are allowed to react with each other in the presence of the salt-forming reagent.

A particularly preferred method resides in refluxing the compounds II and III (X = Cl or Br, $R_1$ = $CH_3$ or $C_2H_5$) for several hours together with an alcoholic (e.g., ethanolic) sodium alcoholate solution.

It is also possible to react a free phenol II with a hydroxy acid derivative of Formula III (X = OH), preferably in the presence of a condensation agent. Suitable condensation agents are, for example, acidic dehydration catalysts, e.g., mineral acids, such as sulfuric acid or phosphoric acid, and also p-toluenesulfonyl chloride, arsenic acid, boric acid, $NaHSO_4$ or $KHSO_4$, and also diaryl carbonates (e.g., diphenyl carbonate), dialkyl carbonates (e.g., dimethyl or diethyl carbonate), or carbodiimides (e.g., dicyclohexylcarbodiimide). If an acid is used as the condensation agent, the reaction is suitably conducted in an excess of this acid without adding another solvent at temperatures of between about $0°$ and about $100°$, preferably between $50°$ and $60°$. However, it is also possible to add a diluent, e.g., benzene, toluene or dioxane. With a carbonic acid ester, the process is preferably conducted at an elevated temperature, suitably between about $100°$ and about $210°$, particularly between $180°$ and $200°$. Optionally, an interesterification catalyst, e.g., sodium carbonate, potassium carbonate or sodium methylate, can also be added.

To produce a compound of Formula I, the phenol II can also be reacted with a haloform (preferably chloroform or bromoform) and a carbonyl compound of the formula $R_2$—CO—$R_3$ (preferably acetone) in the presence of a condensation agent. Especially suitable as a condensation agent is a strong base, such as an alkali metal hydroxide, e.g., NaOH or KOH, which is preferably used in the solid form. This reaction is advantageously effected in the presence of a diluent, e.g., in the presence of an excess of acetone and/or chloroform. Suitably, the reaction is conducted at temperatures of between about $20°$ and about $150°$ preferably at the boiling temperature of the reaction mixture. The reaction times range generally between 3 and 40 hours.

Compounds of Formula I can also be obtained by the cyclization of compounds of Formula IV according to methods known in the literature.

The starting compounds of Formula IV are obtainable according to methods known from the literature. Thus, the amino compounds IV [Z = $Z_1$—$Y_1$—NH—$(A_1)_n$—] can be prepared, for example, by reacting a compound of the formula $Z_1$—$Y_1$—$Z_1$ (wherein $Y_1$ and $Z_1$ have the aforedescribed meanings, e.g., 1,5-dichloro-, 1,5-dibromo-, or 1,5-diiodopentane, o-xylylene chloride, o-xylylene bromide, o-xylylene iodide, phthalyl alcohol and the reactive esters thereof, e.g., the bismethansulfonate or bis-p-toluenesulfonate, o-xylylene diamine, phthalan [=isocoumaran], isoindoline) with a compound of the formula $H_2N$—$(A_1)_n$—(p—$C_6H_4$)—O—$CR_2R_3$—$COOR_1$ (Formula X, wherein $R_1$, $R_2$, $R_3$, $A_1$ and $n$ have the above-indicated meanings).

Suitable solvents for the cyclization of these starting materials [IV, Z = $Z_1$—$Y_1$—NH—$(A_1)_n$—] are, for example, water; lower aliphatic alcohols, e.g., methanol, ethanol, isopropanol, n-butanol; glycols, e.g., ethylene glycol; ethers, e.g., diethyl or diisopropyl ether, THF, dioxane; aliphatic or aromatic hydrocarbons, e.g., hexane, benzene, toluene, xylene; halogenated hydrocarbons, e.g., chloroform, chlorobenzene; nitriles, e.g., acetonitrile; amides, e.g., DMF, dimethylacetamide; sulfoxides, e.g., dimethyl sulfoxide; and mixtures of these solvents. Normally, the cyclization is carried out at temperatures of between about $0°$ and about $300°$, preferably between room temperature and the boiling temperature of the solvent employed. The selection of the catalyst is dependent on the type of the compound $HZ_1$ to be split off. When $Z_1$ is halogen, inorganic or organic bases are preferred, e.g., alkali metal or alkaline earth metal hydroxides, carbonates or alcoholates, tertiary bases, e.g., triethylamine, pyridine, picolines or quinoline. When $Z_1$ is OH, alkoxy, acyloxy, alkyl- or arylsulfonyloxy, however, acidic catalysts are advantageous, e.g., inorganic or organic acids, for example, sulfuric acid, polyphosphoric acid, hydrobromic acid, hydrochloric acid, formic, acetic, propionic, or p-toluenesulfonic acid, which in an excess can likewise serve as the solvent. Compounds wherein $Z_1$ is $NH_2$ split off ammonia during heating, e.g., during melting, thus producing the desired compounds of Formula I.

In a preferred mode of operation, the compounds of Formula IV [Z = $Z_1$—$Y_1$—NH—$(A_1)_n$—] are not isolated but are produced in the nascent state in the presence or absence of an additional solvent and cyclized directly in the thus-obtained reaction mixture.

The reaction of a compound of the formula Br—$Y_1$—Br with an amine of Formula X is especially advantageous in a boiling alcohol in the presence of potassium carbonate, thus obtaining, as an intermediate product, a compound of Formula IV ($Z_1$ 32 Br) which is cyclized in situ. Under these conditions, the reaction is terminated after about 1-12 hours. If desired, unreacted primary (Formula X) and/or secondary (Formula IV) amino compounds can be converted, prior to further processing, into compounds which are not basic by means of acylation, e.g., by treatment with acetic anhydride.

The compounds IV [Z = $Z_2$—$CH_2CH_2$—$N(C_6H_5)$—] can be obtained, for example, from the corresponding diphenylamines of the formula $C_6H_5NH$—(p—$C_6H_4$)—O—$CR_2R_3$—$COOR_1$ with β-propiolactone or derivatives of acrylic acid, as well as by an optionally subsequently conducted functional modification of the $Z_2$ group. Acids of Formula IV ($Z_2$ = COOH) can be cyclized in accordance with methods known in the literature with a dehydration agent, e.g., $ZnCl_2$, polyphosphoric acid, or $SnCl_4$. Also functional derivatives of these acids, e.g., the halogenides thereof, especially the chlorides thereof and also the anhydrides, nitriles or esters thereof, for example, can be cyclized, preferably in the presence of an acidic catalyst, such as $AlCl_3$, $H_2SO_4$ or $BF_3$. The cyclization is normally accomplished at temperatures of between about 0° and about 250°, preferably between 20° and 200°, especially between 75° and 150°. The presence of an additional solvent, e.g., acetic acid, acetic anhyride or nitrobenzene, can be advantageous, but is not required, especially if the cyclizing agent serves simultaneously as the solvent.

Compounds of Formula IV (Z = $C_6H_5$—$Y_2$—$CH_2Ch_2$—CHX—, obtainable, for example, by Friedel-Crafts acylation of compounds of Formula VII ($X_2$ = H) with 3-chloropropionyl chloride, subsequent reaction with sodium phenolate, sodium phenyl mercaptide, or diphenylamine and reduction of the keto group) can be cyclized by intramolecular Friedel-Crafts alkylation, suitably in the presence of an acidic catalyst, e.g., HF, HCl, HBr, $AlCl_3$, $FeCl_3$ or $SnCl_4$ and in the presence of an inert solvent, e.g., carbon disulfide, nitrobenzene or chlorobenzene, or also in the presence of an excess of the cyclizing agent, e.g., concentrated aqueous HBr solution at temperatures of between 0° and 200°, preferably between 20° and 150°.

Compounds of Formula IV [Z = $HY_2$—(o—$C_6H_4$—)—$CH(CH_2CH_2X)$—, obtainable by condensation of a 2—$Y_2H$—4'-hydroxybenzophenone with malonic acid, stepwise reduction to the saturated alcohol, and reaction with compounds of Formula III] are suitably cyclized in the presence of an alkaline catalyst, e.g., alkali metal alcoholates, such as sodium ethylate, or alkali metal hydrides, such as NaH in inert solvents, such as methanol, ethanol or DMF at temperatures of between about 0° and about 120°, preferably between 20° and 80°.

Compounds of Formula I are also obtainable in accordance with methods described in the literature by solvolysis (preferably hydrolysis) of compounds of Formula V wherein W is one of the following groups (wherein the $R_6$ and $R_7$ groups which are to be split off can be an organic group, but especially are alkyl of 1-4 carbon atoms, preferably methyl or ethyl, which can be alike or different but also collectively can be tetramethylene or pentamethylene, optionally interrupted by O); $CHal_3$ (wherein Hal is Cl, Br, or I); COHal; $COOR_8$ (wherein $R_8$ is a group different from $R_1$, particularly alkyl of 5-12 carbon atoms or a substituted alkyl residue which, however, differs from A); $C(OR_6)_3$; COOAcyl [wherein Acyl is the acyl radial of a carboxylic acid of up to 25 carbon atoms, preferably an acid of Formula I ($R_1$ = H)]; CN; $CONH_2$; $CONHR_6$; $CONR_6R_7$; CONHOH; C(OH)=NOH; $CONHNH_2$; $CON_3$; $C(OR_6)$=NH; $C(NH_2)$=$NNH_2$; $C(NHNH_2)$=NH; CSOH; COSH; $CSOR_6$; $CSNH_2$; $CSNHR_6$; or $CSNR_6R_7$. Preferably, W is nitrile or acid amide. Compounds of Formula V are obtainable, for example, by the reaction of phenols of Formula II with acetic acid derivatives of the formula X—$CR_2R_3$—W.

Compounds of Formula V can be solvolyzed in an acidic or alkaline medium at temperatures of between about −20° and 300°, preferably at the boiling temperature of the selected solvent. Suitable acidic catalyst are, for example, hydrochloric, sulfuric, phosphoric, or hydrobromid acid. Examples of suitable basic catalysts are sodium, potassium, or calcium hydroxide, sodium or potassium carbonate. Preferred solvents are water; lower alcohols, such as methanol, ethanol; ethers, such as THF, dioxane; amides, such as DMF; nitriles, such as acetonitrile; sulfones, such as tetramethylenesulfone; and mixtures thereof, especially the water-containing mixtures. The preferred hydrolysis of nitriles (V, W = CN) and acid amides (V, W = $COHN_2$, $CONHR_6$ or CONRhd $6R_7$) is advantageously conducted in an acidic medium (e.g., with acetic acid/hydrochloric acid) or in an alkaline medium (e.g., with ethanolic KOH).

Compounds of Formula I can also be produced according to methods known from the literature by the reaction of compounds of Formula VI with compounds of Formula VII. Starting compounds VI and VII are known and are obtained in accordance with methods described in the literature.

More specifically, it is possible, for example, to react N-haloamines of Formula VI ($X_1$ = Cl or Br), such as N-chloro-1,2,3,4-tetrahydro-4-quinolone, N-chloro-1,2,3,4-tetrahydro-4-hydroxyquinoline, or the corresponding N-bromo compounds or the corresponding reactive derivatives of N-hydroxy compounds, e.g., N-hydroxy-1,2,3,4-tetrahydro-4-quinolone-O-sulfonic acid, with carboxylic acid derivatives of Formula VII ($X_2$ = H), e.g., phenoxyacetic acid, α-phenoxyisobutyric acid, or α-p-chlorophenyl-α-phenoxyacetic acid, or the esters of these acids, preferably in the presence of a catalyst, e.g., metallic salts, such as iron(II) sulfate, $AlCl_3$, $BF_3$ or $ZnCl_2$, in a inert solvent, such as $CS_2$, nitrobenzene, 1,2-dichloroethane, or, with the use of $FeSO_4$, in concentrated or aqueous sulfuric acid. In this mode of operation, the reaction temperatures are advantageously between about −20° and about +60°, preferably between 0° and 40°.

The free amines of Formula VI ($X_1$ = H), e.g., 1,2,3,4-tetrahydro-4-quinolone and 1,2,3,4-tetrahydro-4-hydroxyquinoline, can be reacted with amino compounds of Formula VII ($X_2$ = $NH_2$), e.g., α-p-aminophenoxyacetic acid, α-p-aminophenoxyisobutyric acid, and α-p-aminophenoxy-α-p-chlorophenylacetic acid or the esters thereof, preferably under pressure and with an excess of the amine VI as the solvent, and/or in the presence of an additional inert solvent, as well as an acidic catalyst, such as HCl or p-toluenesulfonic acid or Friedel-Crafts catalyst, such as $AlCl_3$ at temperatures of between about 50° and about 300°, preferably between 150° and 250°.

Metal derivatives, especially the Na-derivatives, of the aforementioned amines of Formula VI ($X_1$ 32 H), can be reacted with halo or sulfonic acid derivatives of Formula VII ($X_2$ = Cl, Br, I or $SO_3M$), e.g., α-p-bromophenoxyacetic acid, α-p-bromophenoxyisobutyric acid, α-p-bromophenoxy-α-p-chlorophenylacetic acid, α-p-sulfophenoxyacetic acid, and the salts and/or esters thereof, preferably in the presence of an excess of the base VI as the solvent and/or in the presence of an additional inert solvent or suspension agent, such as benzene, dioxane, DMF, or HMPA, at temperatures of between 50° and 200°, optionally under pressure and/or an inert gas atmosphere. The metal derivatives of the amines VI can also be produced in situ, e.g., with NaH or $NaNH_2$.

Compounds of Formula I can also be obtained according to methods described in the literature by reduction of the corresponding 3-chromene-, 3-thiochromene- and 1,2-dihydroquinoline derivatives of Formula VIII.

The reduction of these starting substances can suitably be accomplished by catalytic hydrogenation or by chemical processes. The starting compounds can be treated, for example, in the presence of a catalyst, with hydrogen under pressures of between 1 and about 200 atmospheres and at temperatures of between about −80° and 200°, preferably between 20° and 100°. The hydrogenation is advantageously effected in the presence of an inert solvent, e.g., a lower alcohol, such as methanol, ethanol or isopropanol or an ether, such as dioxane. For purposes of hydrogenation, the free compounds of Formula VIII can be utilized, or the corresponding salts, for example the sodium salts of the carboxylic acids VIII ($R_1 32 H$). Examples of suitable catalysts are the noble metal, nickel and cobalt catalysts. The noble metal catalyst can be present on a support (e.g., on carbon, calcium carbonate or strontium carbonate), as oxide catalysts, or as finely divided metallic catalysts. Platinum or palladium is preferably utilized.

Reduction of the compounds VIII can also be accomplished by chemical methods, e.g., with nascent hydrogen, which can be produced, for example, from sodium or sodium amalgam in an alcoholic solution. In this reduction method, temperatures of between about 0° and about 150° are employed.

The starting compounds of Formula VIII can be obtained, for instance, by reacting 4-chromanone or 4-thiochromanone or 1-phenyl-1,2,3,4-tetrahydro-4-quinolinone with compounds otherwise corresponding to Formula VII but having a metal M in place of $X_2$, e.g., p-(2-carboxy-2-propoxy)-phenyllithium. During this reaction, the corresponding carbinols are first produced, which can, however, be dehydrated to the compounds of Formula VIII extremely readily. In fact, these latter compounds are normally formed during the working-up operation.

The phenoxyacetic acid derivatives I ($R_4 = Q$) are also obtained by the alkylation of the acid derivatives IX. These are, in part, known. They can be produced, for example, by reacting the phenols II with compounds of the formula $Z-CHR_3-COOR_1$ under the conditions set forth above for the reaction of compounds II with compounds III.

Suitable for the alkylation of IX are, for example, the following alkylation agents: alkyl halides, such as methyl chloride, bromide, iodide, ethyl chloride, bromide, iodide, and the aryl sulfonates and alkyl sulfates, e.g., methyl p-toluenesulfonate and dimethyl sulfate. Prior to the alkylation, the compounds IX are suitably converted into a metal derivative thereof, e.g., by reaction with an alcoholate, such as sodium ethylate or potassium tert.-butylate, a metal hydride, such as sodium hydride, a metal amide, such as sodium amide or lithium diisopropylamide, an organometallic compound, such as n-butyllithium, or a metal, such as sodium (e.g., in liquid ammonia). This conversion takes place suitably in an inert solvent, e.g., an alcohol, such as methanol, ethanol or tert.-butanol, an ether, such as diethyl ether, an amide, such as DMF or HMPA or a hydrocarbon, such as benzene, and in mixtures of these solvents. The reaction with the alkylating agent is advantageously effected subsequently in the same reaction mixture. The reaction temperatures range normally between about $-20°$ and $+120°$, preferably between about 0° and 80°, and the reaction times range between about 1 hour and 48 hours.

If desired, the $R_1$ groups in a thus-obtained compound of Formula I can be converted into another $R_1$ group in accordance with methods disclosed in the literature by esterification, transesterification or solvolysis.

For example, it is possible to esterify a thus-produced acid of Formula I ($R_1 = H$) with an alcohol of the formula A—OH, suitably in the presence of an inorganic or organic acid, such as HCl, HBr, HI, $H_2SO_4$, $H_3PO_4$, trifluoroacetic acid, benzenesulfonic acid, or p-toluenesulfonic acid or in the presence of an acidic ion exchanger, optionally in the presence of an inert solvent, such as benzene, toluene or xylene, at temperatures of between about 0° and preferably the boiling temperature. The alcohol is preferably used in large molar excess. The esters can also be obtained by chemically adding the carboxylic acids I ($R_1 = H$) to olefins (e.g., isobutylene) or by reacting the carboxylic acids with diazoalkanes, e.g., diazomethane. Furthermore, the esters can be prepared by reacting metallic salts of the acids I ($R_1 = H$), preferably the alkali metal, lead or silver salts, with halogenides of the formula A—Hal or with corresponding chlorosulfites of the formula A—O-SOCl, and the thus-produced adducts are thereafter thermally decomposed. The esterification can also be conducted in several stages. For example, it is possible first to produce from the acid I ($R_1 = H$) the corresponding acid halogenide, e.g., the acid chloride, and react the latter with the alcohol A—OH, optionally in the presence of an acidic or basic catalyst.

Furthermore, the desired esters of Formula I ($R_1 = A$) can be obtained by transesterification, especially by reacting other esters with an excess of the respective alcohol or by reacting the carboxylic acids I ($R_1 = H$) with any desired other ester of the respective alcohol (preferably alkanoates, wherein the alkanoyl residue has up to 4 carbon atoms), especially in the presence of basic or acidic catalysts, e.g., sodium ethylate or sulfuric acid, and at temperatures of between about 0° and preferably the boiling temperature.

It is also possible, in a thus-obtained compound of Formula I, to convert the $R_1$ group by treatment with solvolyzing agents, into another $R_1$ group, especially saponifying a thus-produced ester of Formula I ($R_1 = A$) to the corresponding acid I ($R_1 = H$). The solvolysis and/or saponification can be accomplished in accordance with one of the methods indicated above for the solvolysis of the compounds of Formula V. Preferably, the esters are saponified by treatment with alcoholic alkali solutions, e.g., ethanolic potassium hydroxide, at temperatures of between about 20° and 120°, preferably at the boiling point of the solution.

Oxo compounds obtained in this manner can be reduced to the corresponding hydroxy compounds by treatment with a reducing agent, preferably a complex metal hydride, in accordance with methods known per se from the literature. Suitable reducing agents are sodium borohydride in methanol or ethanol, optionally in the presence of $AlCl_3$ or LiBr. The reaction is effected in an inert solvent, e.g., a lower alcohol, ether, THF or ethylene glycol dimethyl ether. The reaction temperatures range between about 0° and 120°. Preferably, the process is conducted at room temperature, but the reaction can also be terminated by boiling the reaction mixture.

Conversely, a thus-obtained hydroxy compound can be converted into the corresponding oxo compound by treatment with an oxidizing agent. A large number of methods known from the literature can be utilized for this purpose. Preferably, the oxidation is accomplished with dimethyl sulfoxide, together with a dehydration agent, e.g., dicyclohexylcarbodiimide, or with $CrO_3$ in an organic solvent, for example, dimethylformamide or acetic acid.

A basic compound of Formula I can be converted into an acid addition salt thereof with an acid. Suitable are acids forming pharmaceutically acceptable, i.e., physiologically acceptable, salts. Thus, advantageous are organic and inorganic acids, e.g., aliphatic, alicyclic, araliphatic, aromatic or heterocyclic mono- or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, aminocarboxylic acids, sulfamic acid, benzoic acid, salicyclic acid, phenylpropionic acid, citric acid, gluconic acid, ascorbic acid, nicotinic acid, isonicotinic acid, methanesulfonic acid, ethanedisulfonic acid, 2-hydroxyethanesulfonic acid, p-toluenesulfonic acid, naphthalene-mono- and -disulfonic acids, sulfuric acid, nitric acid, hydrohalic acids, such as hydrochloric acid or hydrobromic acid or phosphoric acids, such as orthophosphoric acid.

Similarly, acids of Formula I ($R_1 = H$) can be converted into one of the physiologically acceptable metal and/or ammonium salts thereof by reaction with a base. Examples of suitable salts are the sodium, potassium, magnesium, calcium, ammonium salts and substituted ammonium salts, such as, for example, the dimethyl-, diethyl- and diisopropyl-ammonium, monoethanol-, diethanol-, and triethanolammonium, cyclohexylammoniun, dicyclohexylammonium and dibenzylethylenediammonium salts.

Conversely, compounds of Formula I can be liberated from the acid addition salts thereof by treatment with strong bases and/or from the metal and ammonium salts thereof by treatment with acids.

The compounds of Formula I can contain one or more centers of asymmetry and are ordinarily present in the racemic form. The racemates can be separated into their optical antipodes with the aid of conventional methods as indicated in the literature. Futhermore, it is, of course, possible to obtain optically active compounds in accordance with the above-described methods, by the use of starting substances which are already optically active.

The compounds of Formula I possess with good compatibility, valuable pharmacological properties, including cholesterol-level-lowering, as well as triglyceride-level-lowering, uric-acid-level-lowering and liver-enzyme-inducing activity. This can be demonstrated in accordance with methods known for this purpose. See, e.g., Levine et al., "Automation in Analytical Chemistry," Technicon Symposium, 1967, Mediad, N.Y., pp. 25-28; (lowering of cholesterol level); and Noble and Campbell, Clin. Chem., Vol. 16, 1970, pp. 166-170; (lowering of triglyceride level), in each case in the rat serum.

The compounds of Formula I and the physiologically acceptable salts can be used as drugs and also as intermediates for the production of other medicines.

The compounds of Formula I and/or optionally the physiologically acceptable salts thereof can be employed as drugs in the human or veterinary medicine in admixture with a pharmaceutically acceptable carrier, viz., solid, liquid and/or semiliquid excipients and, if desired, in combination with other effective agents. Suitable vehicles are those organic or inorganic substances suitable for parenteral, enteral or topical application and which do not react with the novel compounds, such as, for example, water, vegetable oils, benzyl alcohols, polyethylene glycols, gelatin, lactose, amylose, magnesium stearate, talc, vaseline, cholesterol. Suitable for parenteral application are, in particular, solutions, preferably oily or aqueous solutions, as well as suspensions, emulsions or implants. For enteral application, suitable are tablets, dragees, capsules, syrups, elixirs or suppositories, and for topical application ointments, creams or powders. The above-indicated preparations can optionally be sterilized or can contain auxiliary agents, such as lubricants, preservatives, stabilizers or wettings agents, emulsifiers, salts to influence the osmotic pressure, buffer substances, coloring, flavoring and/or aromatic substances.

The compounds are preferably administered in doses of between 10 and 1000 mg. per dosage unit. Oral administration is preferred, particularly in doses of between 50 and 500 mg. per dosage unit.

In test animals, particularly in rats, the activities occurred when doses of about 10 to 100 mg./kg. were applied. Other suitable test animals are, f.e., mice, rabbits, guinea pigs, dogs, monkeys and pigs.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The temperatures set forth herein are in degrees Celsius.

PREPARATION a. 23 g. of 4-hydroxydiphenylamine are heated to 130°. After addition of 0.56 g of zinc chloride, the mixture is heated to 150° and 9.4 g. of β-propiolactone are added dropwise. The mixture is stirred for 15 minutes, cooled and taken up in ethylacetate. By extraction with dilute sodium hydroxide solution and acidification 3-[N-phenyl-N-(4-hydroxyphenyl)-amino]propionic acid of m.p. 173°-175° is obtained.

b. A mixture of 30 g. of this acid, 800 ml of acetic acid and 55 ml. of acetic anhydride is warmed to 90°. A solution of 16 g. of zinc chloride in 165 ml. of acetic anhydride is added, the resulting mixture is boiled for 10 minutes, cooled, and poured into water. After extraction with ether and usual working up, 1-(4-acetoxyphenyl)-4-oxo-1,2,3,4-tetrahydroquinoline (A) of m.p. 130° - 132° is obtained (from ethanol).

c. Conventional alkaline saponification of compound A [method see Example 1b), below] yields 1-p-hydroxyphenyl-1,2,3,4-tetrahydro-4-quinolone; m.p. 190° - 192°.

d. Conventional sodium borohydride reduction of compound A [method see Example 2c), below] yields 1-p-hydroxyphenyl-4-hydroxy-1,2,3,4-tetahydro-quinoline.

e. Conventional Wolff-Kishner reduction of compound A [method see Organic Reactions IV, 378 (1948)] yields 1-p-hydroxyphenyl-1,2,3,4-tetrahydroquinoline, m.p. 112° - 114°.

EXAMPLE 1 a. 2.3 g. of sodium is dissolved in 100 ml. of absolute ethanol; 17.7 g. of 4-piperidinophenol is introduced into the solution, and then 24.3 g. of ethyl α-bromophenylacetate is added dropwise thereto and the mixture refluxed for 10 hours. The reaction mixture is then evaporated, the residue mixed with water, and the aqueous solution extracted with ethyl acetate. The ethyl acetate solution is washed twice with dilute KOH and twice with water, then dried, and the solvent is evaporated, thus obtaining the ethyl ester of α-phenyl-α-4- piperidinophenoxy-acetic acid; hydrochloride, m.p. 149°–151°.

Analogously, the following compounds are produced with ethyl α-bromophenylacetate from the corresponding phenols of Formula II:

ethyl ester of α-phenyl-α-4-isoindolinophenoxyacetic acid, m.p. 132°
ethyl ester of α-phenyl-α-4-(1,2,3,4-tetrahydroquinolino)-phenoxyacetic acid, m.p. 96°–98°
ethyl ester of α-phenyl-α-4-(1,2,3,4-tetrahydro-4-quinolyl)-phenoxyacetic acid
ethyl ester of α-phenyl-α-4-(1-methyl-1,2,3,4-tetrahydro-4-quinolyl)-phenoxyacetic acid, oil, $n_D^{20}$ 1.5950
ethyl ester of α-phenyl-α-4-(4-piperidinophenyl)-phenoxyacetic acid, m.p. 126°–128°
ethyl ester of α-phenyl-α-4-(4-piperidinophenoxy)-phenoxyacetic acid
ethyl ester of α-phenyl-α-4-(1-pyrryl)-phenoxyacetic acid.

Analogously, the following products are obtained with the ethyl ester of 2-chloropropionic acid, the ethyl ester of α-bromo-α-(o-chlorophenyl)-acetic acid, the ethyl of α-bromo-α-(m-chlorophenyl)-acetic acid, and the ethyl ester of α-bromo-α-(p-chlorophenyl)-acetic acid:

the ethyl ester of each of the following acids, respectively:

α-4-piperidinophenoxypropionic acid
α-4-isoindolinophenoxypropionic acid
α-4-(1,2,3,4-tetrahydroquinolino)-phenoxypropionic acid
α-4-(1,2,3,4-tetrahydro-4-quinolyl)-phenoxypropionic acid
α-4-(1-methyl-1,2,3,4-tetrahydro-4-quinolyl)-phenoxypropionic acid
α-4-(4-piperidinophenyl)-phenoxypropionic acid
α-4-(4-piperidinophenoxy)-phenoxypropionic acid
α-4-(1-pyrryl)-phenoxypropionic acid
α-o-chlorophenyl-α-4-piperidinophenoxyacetic acid
α-o-chlorophenyl-α-4-isoindolinophenoxyacetic acid
α-o-chlorophenyl-α-4-(1,2,3,4-tetrahydroquinolino)-phenoxyacetic acid
α-o-chlorophenyl-α-4-(1,2,3,4-tetrahydro-4-quinolyl)-phenoxyacetic acid
α-o-chlorophenyl-α-4-(1-methyl-1,2,3,4-tetrahydro-4-quinolyl)-phenoxyacetic acid
α-o-chlorophenyl-α-4-(4-piperidinophenyl)-phenoxyacetic acid
α-o-chlorophenyl-α-4-(4-piperidinophenoxy)-phenoxyacetic acid
α-o-chlorophenyl-α-4-(1-pyrryl)-phenoxyacetic acid
α-m-chlorophenyl-α-4-piperidinophenoxyacetic acid; hydrochloride, m.p. 149°–151°
α-m-chlorophenyl-α-4-isoindolinophenoxyacetic acid
α-m-chlorophenyl-α-4-(1,2,3,4-tetrahydroquinolino)-phenoxyacetic acid
α-m-chlorophenyl-α-4-(1,2,3,4-tetrahydro-4-quinolyl)-phenoxyacetic acid
α-m-chlorophenyl-α-4-(1-methyl-1,2,3,4-tetrahydro-4-quinolyl)-phenoxyacetic acid
α-m-chlorophenyl-α-4-(4-piperidinophenyl)-phenoxyacetic acid, m.p. 96°–97°
α-m-chlorophenyl-α-4-(4-piperidinophenoxy)-phenoxyacetic acid
α-m-chlorophenyl-α-4-(1-pyrryl)-phenoxyacetic acid
α-p-chlorophenyl-α-4-piperidinophenoxyacetic acid
α-p-chlorophenyl-α-4-isoindolinophenoxyacetic acid
α-p-chlorophenyl-α-4-(1,2,3,4-tetrahydroquinolino)-phenoxyacetic acid, oil, $n_D^{20}$ 1.6129
α-p-chlorophenyl-α-4-(1,2,3,4-tetrahydro-4-quinolyl)-phenoxyacetic acid
α-p-chlorophenyl-α-4-(1-methyl-1,2,3,4-tetrahydro-4-quinolyl)-phenoxyacetic acid
α-p-chlorphenyl-α-4-(4-piperidinophenyl)-phenoxyacetic acid, m.p. 122°
α-p-chlorophenyl-α-4-(4-piperidinophenoxy)-phenoxyacetic acid
α-p-chlorophenyl-α-4-(1-pyrryl)-phenoxyacetic acid, m.p. 109°.

b. 3.39 g. of the ethyl ester of α-phenyl-α-4-piperidinophenoxyacetic acid is refluxed for 2 hours with 3 g. of KOH in 30 ml. of ethanol. The mixture is then evaporated, mixed with water, extracted with ether, and hydrochloric acid is added to pH 4. The thus-obtained α-phenyl-α-4-piperidinophenoxyacetic acid is filtered.

Analogously, the following compounds are produced by saponification of the corresponding ethyl esters:

α-phenyl-α-4-isoindolinophenoxyacetic acid
α-phenyl-α-4-(1,2,3,4-tetrahydroquinolino)-phenoxyacetic acid; diisopropylamine salt, m.p. 169°–171°
α-phenyl-α-4-(1,2,3,4-tetrahydro-4-quinolyl)-phenoxyacetic acid; cyclohexylamine salt, m.p. 241°–243°
α-phenyl-α-4-(1-methyl-1,2,3,4-tetrahydro-4-quinolyl)-phenoxyacetic acid; diisopropylamine salt, m.p. 165°–168°
α-phenyl-α-4-(4-piperidinophenyl)-phenoxyacetic acid
α-phenyl-α-4-(4-piperidinophenoxy)-phenoxyacetic acid
α-phenyl-α-4-(1-pyrryl)-phenoxyacetic acid
α-4-piperidinophenoxypropionic acid
α-4-isoindolinophenoxypropionic acid
α-4-(1,2,3,4-tetrahydroquinolino)-phenoxypropionic acid
α-4-(1,2,3,4-tetrahydro-4-quinolyl)-phenoxypropionic acid
α-4-(1-methyl-1,2,3,4-tetrahydro-4-quinolyl)-phenoxypropionic acid; cyclohexylamine salt, m.p. 203°–205°
α-4-(4-piperidinophenyl)-phenoxypropionic acid, m.p. 215°
α-4-(4-piperidinophenoxy)-phenoxypropionic acid, m.p. 160°–162°
α-4-(1-pyrryl)-phenoxypropionic acid
α-o-chlorophenyl-α-4-piperidinophenoxyacetic acid
α-o-chlorophenyl-α-4-isoindolinophenoxyacetic acid
α-o-chlorophenyl-α-4-(1,2,3,4-tetrahydroquinolino)-phenoxyacetic acid
α-o-chlorophenyl-α-4-(1,2,3,4-tetrahydro-4-quinolyl)-phenoxyacetic acid
α-o-chlorophenyl-α-4-(1-methyl-1,2,3,4-tetrahydro-4-quinolyl)-phenoxyacetic acid
α-o-chlorophenyl-α-4-(4-piperidinophenyl)-phenoxyacetic acid
α-o-chlorophenyl-α-4-(4-piperidinophenoxy)-phenoxyacetic acid
α-o-chlorophenyl-α-4-(1-pyrryl)-phenoxyacetic acid
α-m-chlorophenyl-α-4-piperidinophenoxyacetic acid, m.p. 185°–190°
α-m-chlorophenyl-α-4-isoindolinophenoxyacetic acid
α-m-chlorophenyl-α-4-(1,2,3,4-tetrahydroquinolino)-phenoxyacetic acid α-m-chlorophenyl-α-4-(1,2,3,4-tetrahydro-4-quinolyl)-phenoxyacetic acid α-m-chlorophenyl-α-4-(1-methyl-1,2,3,4-tetrahydro-4-quinolyl)-phenoxyacetic acid α-m-chlorophenyl-α-4-(4-piperidinophenyl)-phenoxyacetic acid α-m-chlorophenyl-α-4-(4-piperidinophenoxy)-phenoxyacetic acid α-m-chlorophenyl-α-4-(1-pyrryl)-phenoxyacetic acid α-p-chlorophenyl-α-4-piperidinophenoxyacetic acid, m.p. 173°-175°

α-p-chlorophenyl-α-4-isoindolinophenoxyacetic acid

α-p-chlorophenyl-α-4-(1,2,3,4-tetrahydroquinolino)-phenoxyacetic acid; diisopropylamine salt, m.p. 155°-158°

α-p-chlorophenyl-α-4-(1,2,3,4-tetrahydro-4-quinolyl)-phenoxyacetic acid

α-p-chlorophenyl-α-4-(1-methyl-1,2,3,4-tetrahydro-4-quinolyl)-phenoxyacetic acid; diisopropylamine salt, m.p. 174°-181°

α-p-chlorophenyl-α-4-(4-piperidinophenyl)-phenoxyacetic acid

α-p-chlorophenyl-α-4-(4-piperidinophenoxy)-phenoxyacetic acid; cyclohexylamine salt, m.p. 240°-242°

α-p-chlorophenyl-α-4-(1-pyrryl)-phenoxyacetic acid.

EXAMPLE 2 a. Analogously to Example 1(a), the methyl ester of 2-methyl-2-p-(4-oxo-1,2,3,4-tetrahydroquinolino)-phenoxypropionic acid, m.p. 76°-78° (from hexane), is obtained from 1-p-hydroxyphenyl-1,2,3,4-tetrahydro-4-quinolone and the methyl ester of α-bromoisobutyric acid in absolute methanol in the presence of sodium methylate (48 hours).

In an analogous manner, the following compounds are obtained from 1-p-hydroxyphenyl-1,2,3,4-tetrahydro-4-quinolone and 1-p-hydroxyphenyl-4-hydroxy-1,2,3,4-tetrahydroquinoline with the methyl and ethyl esters, respectively, of bromoacetic acid, α-bromopropionic acid, α-bromobutyric acid, α-bromoisobutyric acid, α-bromocaproic acid, α-bromophenylacetic acid, α-bromo-α-o-chlorophenylacetic acid, α-bromo-α-m-chlorophenylacetic acid and α-bromo-α-p-chlorophenylacetic acid:

methyl ester of α-p-(4-oxo-1,2,3,4-tetrahydroquinolino)-phenoxyacetic acid, ethyl ester of α-p-(4-oxo-1,2,3,4-tetrahydroquinolino)-phenoxyacetic acid, the methyl ester and the ethyl ester of α-p-(4-oxo-1,2,3,4-tetrahydroquinolino)-phenoxypropionic acid, the methyl ester and the ethyl ester of α-p-(4-oxo-1,2,3,4-tetrahydroquinolino)-phenoxybutyric acid, the ethyl ester of 2-methyl-2-p-(4-oxo-1,2,3,4-tetrahydroquinolino)-phenoxypropionic acid, the methyl ester and the ethyl ester of α-p-(4-oxo-1,2,3,4-tetrahydroquinolino)-phenoxycaproic acid, the methyl ester and the ethyl ester of α-phenyl-α-p-(4-oxo-1,2,3,4-tetrahydroquinolino)-phenoxyacetic acid, methyl ester of 2-phenyl-2-p-(4-oxo-1,2,3,4-tetrahydroquinolino)-phenoxypropionic acid, the ethyl ester of 2-phenyl-2-p-(4-oxo-1,2,3,4-tetrahydroquinolino)-phenoxypropionic acid, oil, $n_D^{20}$ 1.5898, the methyl ester and the ethyl ester of α-o-chlorophenyl-α-p-(4-oxo-1,2,3,4-tetrahydroquinolino)-phenoxyacetic acid, the methyl ester and the ethyl ester of α-m-chlorophenyl-α-p-(4-oxo-1,2,3,4-tetrahydroquinolino)-phenoxyacetic acid, the methyl ester and the ethyl ester of α-p-chlorophenyl-α-p-(4-oxo-1,2,3,4-tetrahydroquinolino)-phenoxyacetic acid, the methyl ester and the ethyl ester of α-p-(4-hydroxy-1,2,3,4-tetrahydroquinolino)-phenoxyacetic acid, the methyl ester and the ethyl ester of α-p-(4-hydroxy-1,2,3,4-tetrahydroquinolino)-phenoxypropionic acid, the methyl ester and the ethyl ester of α-p-(4-hydroxy-1,2,3,4-tetrahydroquinolino)-phenoxybutyric acid, the methyl ester and the ethyl ester of 2-methyl-2-p-(4-hydroxy-1,2,3,4-tetrahydroquinolino)-phenoxypropionic acid, the methyl ester and the ethyl ester of α-p-(4-hydroxy-1,2,3,4-tetrahydroquinolino)-phenoxycaproic acid, the methyl ester and the ethyl ester of α-phenyl-α-p-(4-hydroxy-1,2,3,4-tetrahydroquinolino)-phenoxyacetic acid, the methyl ester and the ethyl ester of 2-phenyl-2-p-(4-hydroxy-1,2,3,4-tetrahydroquinolino)-phenoxypropionic acid, the methyl ester and the ethyl ester of α-o-chlorophenyl-α-p-(4-hydroxy-1,2,3,4-tetrahydroquinolino)-phenoxyacetic acid, the methyl ester and the ethyl ester of α-m-chlorophenyl-α-p-(4-hydroxy-1,2,3,4-tetrahydroquinolino)-phenoxyacetic acid, the methyl ester and the ethyl ester of α-p-chlorophenyl-α-p-(4-hydroxy-1,2,3,4-tetrahydroquinolino)-phenoxyacetic acid.

b. Analogously to Example 1(b), 2-methyl-2-p-(4-oxo-1,2,3,4-tetrahydroquinolino)-phenoxypropionic acid is obtained from the methyl ester of 2-methyl-2-p-(4-oxo-1,2,3,4-tetrahydroquinolino)-phenoxypropionic acid with KOH in methanol (4 hours of refluxing).

Analogously, the following final products are obtained by the saponification of the corresponding methyl and ethyl esters, respectively:

α-p-(4-oxo-1,2,3,4-tetrahydroquinolino)-phenoxyacetic acid

α-p-(4-oxo-1,2,3,4-tetrahydroquinolino)-phenoxypropionic acid; cyclohexylamine salt, m.p. 180°

α-p-(4-oxo-1,2,3,4-tetrahydroquinolino)-phenoxybutyric acid

α-p-(4-oxo-1,2,3,4-tetrahydroquinolino)-phenoxycaproic acid

α-phenyl-α-p-(4-oxo-1,2,3,4-tetrahydroquinolino)-phenoxyacetic acid; cyclohexylamine salt, m.p. 170°

2-phenyl-2-p-(4-oxo-1,2,3,4-tetrahydroquinolino)-phenoxypropionic acid; cyclohexylamine salt, m.p. 178°-180°

α-o-chlorophenyl-α-p-(4-oxo-1,2,3,4-tetrahydroquinolino)-phenoxyacetic acid

α-m-chlorophenyl-α-p-(4-oxo-1,2,3,4-tetrahydroquinolino)-phenoxyacetic acid

α-p-chlorophenyl-α-p-(4-oxo-1,2,3,4-tetrahydroquinolino)-phenoxyacetic acid, m.p. 180°-185°

α-p-(4-hydroxy-1,2,3,4-tetrahydroquinolino)-phenoxyacetic acid

α-p-(4-hydroxy-1,2,3,4-tetrahydroquinolino)-phenoxypropionic acid

α-p-(4-hydroxy-1,2,3,4-tetrahydroquinolino)-phenoxybutyric acid 2-methyl-2-p-(4-hydroxy-1,2,3,4-tetrahydroquinolino)-phenoxypropionic acid α-p-(4-hydroxy-1,2,3,4-tetrahydroquinolino)-phenoxycaproic acid α-phenyl-α-p-(4-hydroxy-1,2,3,4-tetrahydroquinolino)-phenoxyacetic acid 2-phenyl-2-p-(4-hydroxy-1,2,3,4-tetrahydroquinolino)-phenoxypropionic acid α-o-chlorophenyl-α-p-(4-hydroxy-1,2,3,4-tetrahydroquinolino)-phenoxyacetic acid α-m-chlorophenyl-α-p-(4-hydroxy-1,2,3,4-tetrahydroquinolino)- phenoxyacetic acid α-p-chlorophenyl-α-p-(4-hydroxy-1,2,3,4-tetrahydroquinolino)-phenoxyacetic acid.

c. A solution of 3.39 g. of the methyl ester of 2-methyl-2-p-(4-oxo-1,2,3,4-tetrahydroquinolino)-phenoxypropionic acid in 40 ml. of methanol is mixed under agitation with 0.4 g. of NaBH₄ and then stirred for 1 hour at 25°. The mixture is then poured into water, extracted with ether, dried, evaporated, and the product thus obtained is the methyl ester of 2-methyl-2-p-(4-hydroxy-1,2,3,4-tetrahydroquinolino)-phenoxypropionic acid.

d. A mixture of 3.41 g. of the methyl ester of 2-methyl-2-p- (4-hydroxy-1,2,3,4-tetrahydroquinolino)-phenoxypropionic acid, 3 g. of dicyclohexylcarbodiimide, 0.8 ml. of pyridine, 0.4 ml. of trifluoroacetic acid, 25 ml. of dimethyl sulfoxide, and 25 ml. of benzene is allowed to stand overnight at 25° . After adding ether thereto, the mixture is filtered, the filtrate diluted with water, and worked up as usual, thus producing the methyl ester of 2- methyl-2-p-(4-oxo-1,2,3,4-tetrahydroquinolino)-phenoxypropionic acid, m.p. 76°-78°.

EXAMPLE 3 a. 2.3 g. of sodium is dissolved in 170 ml. of absolute isopropanol, and 22.6 g. of 4-p-hydroxyphenylchromane (obtainable by reacting 4-chromanol with phenol in the presence of AlCl₃) is introduced into the reaction mixture; 15 g. of the ethyl ester of 2-chloroisobutyric acid is added dropwise and the mixture refluxed for 20 hours. After working the mixture up as usual, the oily ethyl ester of 2-methyl-2-p-(4-chromanyl)-phenoxypropionic acid is obtained.

Analogously, the following compounds are produced from 4-p-hydroxyphenylchromane, 4-p-hydroxyphenylthiochromane (obtainable from 4-hydroxythiochromane) and 1-phenyl-4-(p-hydroxyphenyl)-1,2,3,4-tetrahydroquinoline (obtainable from 1-phenyl-1,2,3,4-tetrahydro-4-hydroxyquinoline), respectively:

the methyl ester and the ethyl ester of 2-p-(4-chromanyl)-phenoxypropionic acid, the methyl ester of 2-methyl-2-p-(4-chromanyl)-phenoxypropionic acid, the methyl ester and the ethyl ester of α-phenyl-α-p-(4-chromanyl)-phenoxyacetic acid, the methyl ester and the ethyl ester of α-o-chlorophenyl-α-p- (4-chromanyl)-phenoxyacetic acid, the methyl ester and the ethyl ester of α-m-chlorophenyl-α-p-(4-chromanyl)-phenoxyacetic acid, the methyl ester and the ethyl ester of α-p-chlorophenyl-α-p- (4-chromanyl)-phenoxyacetic acid, the methyl ester and the ethyl ester of 2-p-(4-thiochromanyl)-phenoxypropionic acid, the methyl ester and the ethyl ester of 2-methyl-2-p-(4-thiochromanyl)-phenoxypropionic acid, the methyl ester and ethyl ester of α-phenyl-α-p-(4-thiochromanyl)-phenoxyacetic acid, the methyl ester and ethyl ester of α-o-chlorophenyl-α-p-(4-thiochromanyl)-phenoxyacetic acid, the methyl ester and ethyl ester of α-m-chlorophenyl-α-p- (4-thiochromanyl)-phenoxyacetic acid, the methyl ester and ethyl ester of α-p-chlorophenyl-α-p- (4-thiochromanyl)-phenoxyacetic acid, the methyl ester and ethyl ester of 2-p-(1-phenyl-1,2,3,4-tetrahydro-4-quinolyl)-phenoxypropionic acid, the methyl ester and ethyl ester of 2-methyl-2-p-(1-phenyl-1,2,3,4-tetrahydro-4-quinolyl)-phenoxypropionic acid, the methyl ester and ethyl ester of α-phenyl-α-p-(1-phenyl- 1,2,3,4-tetrahydro-4-quinolyl)-phenoxyacetic acid, the methyl ester and ethyl ester of α-o-chlorophenyl-α-p-(1-phenyl-1,2,3,4-tetrahydro-4-quinolyl)-phenoxyacetic acid, the methyl ester and ethyl ester of α-m-chlorophenyl-α-p-(1-phenyl-1,2,3,4-tetrahydro-4-quinolyl)-phenoxyacetic acid, the methyl ester and ethyl ester of α-p-chlorophenyl-α-p-(1-phenyl-1,2,3,4-tetrahydro-4-quinolyl)-phenoxyacetic acid.

(b) Analogously to Example 1(b), 2-methyl-2-p-(4-chromanyl)-phenoxypropionic acid is obtained by saponification of the ethyl ester of 2-methyl-2-p-(4-chromanyl)-phenoxypropionic acid. Cyclohexylamine salt, m.p 196°-198°.

In an analogous manner, the following products are obtained by the saponification of the corresponding methyl and ethyl esters, respectively:

2-p-(4-chromanyl)-phenoxypropionic acid

α-phenyl-α-p-(4-chromanyl)-phenoxyacetic acid; cyclohexylamine salt, m.p. 215°-217°

α-o-chlorophenyl-α-p-(4-chromanyl)-phenoxyacetic acid

α-m-chlorophenyl-α-p-(4-chromanyl)-phenoxyacetic acid

α-p-chlorophenyl-α-p-(4-chromanyl)-phenoxyacetic acid 2-p-(4-thiochromanyl)-phenoxypropionic acid 2-methyl-2-p-(4-thiochromanyl)-phenoxypropionic acid; diisopropylamine salt, m.p. 137°-139°

α-phenyl-α-p-(4-thiochromanyl)-phenoxyacetic acid; cyclohexylamine salt, m.p. 239°-241°

α-o-chlorophenyl-α-p-(4-thiochromanyl)-phenoxyacetic acid

α-m-chlorophenyl-α-p-(4-thiochromanyl)-phenoxyacetic acid

α-p-chlorophenyl-α-p-(4-thiochromanyl)-phenoxyacetic acid 2-p-(1-phenyl-1,2,3,4-tetrahydro-4-quinolyl)-phenoxypropionic acid 2-methyl-2-p-(1-phenyl-1,2,3,4-tetrahydro-4-quinolyl)-phenoxypropionic acid; diisopropylamine salt, m.p. 135°-138°

α-phenyl-α-p-(1-phenyl-1,2,3,4-tetrahydro-4-quinoly)-phenoxyacetic acid

α-o-chlorophenyl-α-p-(1-phenyl-1,2,3,4-tetrahydro-4-quinolyl)-phenoxyacetic acid α-m-chlorophenyl-α-p-(1-phenyl-1,2,3,4-tetrahydro-4-quinolyl)-phenoxyacetic acid α-p-chlorophenyl-α-p-(1-phenyl-1,2,3,4-tetrahydro-4-quinolyl)-phenoxyacetic acid.

EXAMPLE 4 a. Analogously to Example 1(a), the following compounds are obtained from the corresponding phenols with 2-bromo-2-phenylpropionic acid ethyl ester:

ethyl ester of 2-phenyl-2-p-(4-chromanyl)-phenoxypropionic acid, oil, $n_D^{20}$ 1.5832
ethyl ester of 2-phenyl-2-p-(4-thiochromanyl)-phenoxypropionic acid, oil, $n_D^{20}$ 1.5969
ethyl ester of 2-phenyl-2-p-(1-phenyl-1,2,3,4-tetrahydro-4-quinolyl)-phenoxypropionic acid.

b. Analogously to Example 1(b), the following products are obtained by saponification of the aforementioned esters:

2-phenyl-2-p-(4-chromanyl)-phenoxypropionic acid; cyclohexylamine salt, m.p. 190°–193°
2-phenyl-2-p-(4-thiochromanyl)-phenoxypropionic acid; cyclohexylamine salt, m.p. 187°–189°; sodium salt, m.p. 200°–202°
2-phenyl-2-p-(1-phenyl-1,2,3,4-tetrahydro-4-quinolyl)-phenoxypropionic acid.

EXAMPLE 5

22.5 g. of 4-(1,2,3,4-tetrahydroquinolino)-phenol is added to a suspension of 2.4 g. of NaH in 200 ml. of dimethylacetamide. The mixture is stirred for one hour at room temperature, maintained at 90° for 20 hours after the addition of 27.75 g. of the ethyl ester of α-bromo-α-p-chlorophenylacetic acid, cooled, mixed with water, and extracted with ether. The ether solution is washed twice with 2N NaOH and evaporated after drying, thus obtaining the ethyl ester of α-p-chlorophenyl-α-4-(1,2,3,4-tetrahydroquinolino)-phenoxyacetic acid. Free acid, diisopropylamine salt, m.p. 155°–158°.

EXAMPLE 6

A mixture of 2.26 g. of 4-p-hydroxyphenylchromane and 0.23 g. of sodium in 50 ml. of xylene is refluxed for 3 hours. The mixture is allowed to cool to 20°; then, 2.57 g. of the ethyl ester of 2-bromo-2-phenylpropionic acid in 10 ml. of xylene is added, the suspension is agitated for 6 hours under boiling heat, cooled, and treated with 2 ml. of ethanol. The inorganic precipitate is filtered off, the filtrate is evaporated, the residue is taken up in ether, the solution is washed with $NaHCO_3$ solution and saturated NaCl solution, dried over $MgSO_4$, and evaporated, thus obtaining the ethyl ester of 2-phenyl-2-p-(4-chromanyl)-phenoxypropionic acid, $n_D^{20}$ 1.5832.

Analogously, with the use of the phenols set forth in Example 1, and reacting same with the propyl, isopropyl, n-butyl, isobutyl, sec.-butyl and tert.-butyl esters, respectively, of α-bromopropionic acid, α-bromoisobutyric acid, α-bromophenylacetic acid, α-bromo-α-o-chlorophenylacetic acid, α-bromo-α-m-chlorophenylacetic acid, and α-bromo-α-p-chlorophenylacetic acid, one obtains the corresponding esters of the acids indicated in Example 1(b), e.g. the n-propyl, isopropyl, n-butyl, isobutyl, sec.-butyl, and tert.-butyl esters of 2-methyl-2-p-(4-chromanyl)-phenoxypropionic acid.

EXAMPLE 7

A solution of 27.75 g. of the ethyl ester of α-bromo-α-p-chlorophenylacetic acid in 50 ml. of acetone is gradually added to an agitated mixture of 25.3 g. of 4-(4-piperidinophenyl)-phenol, 13.8 g. of $K_2CO_3$, and 80 ml. of acetone. The mixture is refluxed under stirring, filtered, and evaporated, thus producing the ethyl ester of α-p-chlorophenyl-α-4-(4-piperidinophenyl)-phenoxyacetic acid, m.p. 122°.

EXAMPLE 8

15 g. of sulfuric acid is added to a mixture of 25.3 g. of 4-(4-piperidinophenyl)-phenol and 21.45 g. of the ethyl ester of α-m-chlorophenylglycolic acid; the reaction mixtue is agitated for 2 hours at 50°–60°. After cooling, the mixtue is combined with water, dilute NaOH is added to pH 8, and the aqueous phase is extracted with ether. The mixture is then dried, evaporated, and the thus-obtained product is the ethyl ester of α-m-chlorophenyl-α-4-(4-piperidinophenyl)-phenoxyacetic acid, m.p. 96°–97°.

EXAMPLE 9 a. 23.9 g. of 4-(1-methyl-1,2,3,4-tetrahydro-4-quinolyl)-phenol is dissolved in 200 ml. of acetone. Under agitation, 4 g. of NaOH is added to the mixture and thereafter, under agitation and boiling, 21.5 g. of α-bromophenylacetic acid (or 17.05 g. of α-chlorophenylacetic acid) is introduced dropwise in 60 ml. of acetone. The mixture is stirred for another hour at 56° and allowed to stand for 24 hours. The acetone is distilled off, the residue is dissolved in 1.1 of water, the solution is washed several times with ether and acidified with HCl to pH 4, thus obtaining α-phenyl-α-4-(1-methyl-1,2,3,4-tetrahydro-4-quinolyl)-phenoxyacetic acid; diisopropylamine salt, m.p. 165°–168°.

b. One gram of α-phenyl-α-4-(1-methyl-1,2,3,4,-tetrahydro-4-quinolyl)-phenoxyacetic acid is dissolved in 20 ml. of ether and mixed dropwise with ether diazomethane solution until the mixture assumes a permanent yellow coloring. After evaporation, the methyl ester of α-phenyl-α-4-(1-methyl-1,2,3,4-tetrahydro-4-quinolyl)-phenoxyacetic acid is obtained.

c. 5 g. of α-phenyl-α-4-(1-methyl-1,2,3,4-tetrahydro-4-quinolyl)-phenoxyacetic acid is dissolved in 200 ml. of saturated ethanolic hydrochloric acid; the mixture is allowed to stand for 12 hours at room temperature, refluxed for 2 hours, and evaporated. The residue is dissolved in water, the aqueous solution is adjusted to pH 8 with 1N NaOH, and extracted with ethyl acetate. The product is dried and evaporated, thus obtaining the ethyl ester of α-phenyl-α-4-(1-methyl-1,2,3,4-tetrahydro-4-quinolyl)-phenoxyacetic acid.

EXAMPLE 10

At 40°, 30 g. of chloroform is added dropwise to a mixture of 23.9 g. of 1-p-hydroxyphenyl-1,2,3,4-tetrahydro-4-quinolone, 80 g. of acetone, and 21 g. of pulverized KOH. The mixture is refluxed for 12 hours, evaporated, the residue mixed with water, washed with ether, acidified to pH 5, and extracted with ether. The ether solution is extracted with dilute sodium carbonate solution, the latter is washed with ether, then again acidified and extracted with ether. The ether extracts are dried over sodium sulfate and evaporated, thus obtaining 2-methyl-2-p-(4-oxo-1,2,3,4-tetrahydroquinolino)-phenoxypropionic acid.

EXAMPLE 11

30.1 g. of the ethyl ester of α-4-(4-aminophenoxy)-phenoxypropionic acid (obtainable by reacting 4-(4-nitrophenoxy)-phenol with the ethyl ester of 2-chloropropionic acid to obtain the ethyl ester of α-4-(4-nitrophenoxy)-phenoxypropionic acid and subsequent reduction of the nitro group), 34.5 g. of 1,5-dibromopentane, and 27 g. of $K_2CO_3$ are refluxed under agitation in 400 ml. of n-butanol for 24 hours. Then, the mixture is filtered, the solvent distilled off, the residue mixed with water and extracted with chloroform. The extract is dried and evaporated, thus producing the ethyl ester of α-4-(4-piperidinophenoxy)-phenoxypropionic acid. Free acid, m.p. 160°–162°.

EXAMPLE 12

A mixture of 23.7 g. of the isobutyl ester of 2-(4-aminophenoxy)-propionic acid, 23 g. of 1,5-dibromopentane, 14 g. of $Na_2CO_3$, and 100 ml. of acetonitrile is refluxed under agitation for 48 hours. The mixtue is filtered, evaporated, the residue taken up in dilute hydrochloric acid, washed with ether, made alkaline with dilute solution of sodium hydroxide, extracted with ether, dried, evaporated, and the product thus obtained is the isobutyl ester of 2-(4-piperidinophenoxy)-propinic acid.

EXAMPLE 13

34.7 g. of the ethyl ester of α-phenyl-α-4-(4-aminophenyl)-phenoxyacetic acid is refluxed in 350 ml. of n-butanol together with 15 g. of 1,5-dichloropentane and 15 g. of pulverized $K_2CO_3$ for 15 hours. The mixture is then cooled, filtered, the butanol is distilled off, the residue dissolved in 150 ml. of benzene and refluxed for 2 hours with 10 ml. of acetic anhydride. The reaction mixture is cooled, washed with 1N NaOH, and extracted with 20% HCl. The aqueous hydrochloric acid solution is rendered alkaline, extracted with ether, the ether phase washed neutral with water, dried, and evaporated, thus obtaining the ethyl ester of α-phenyl-α-4-(4-piperidinophenyl)-phenoxyacetic acid, m.p. 126°–128°.

EXAMPLE 14

A solution of 35.7 g. of the methyl ester of 2-methyl-2-p-(N-2-carboxyethylanilino)-phenoxypropionic acid (obtainable by reacting the methyl ester of 2-methyl-2-(p-anilinophenoxy)-propionic acid with propiolactone) in 800 ml. of acetic acid and 55 ml. of acetic anhydride is combined at 90° with a solution of 16 g. of zinc chloride in 165 ml. of acetic anhydride. The mixture is then refluxed for 10 minutes, immediately poured into 2.5 l. of water, extracted with ether, and the usual working up operation yields the methyl ester of 2-methyl-2-p-(4-oxo-1,2,3,4-tetrahydroquinolino)-phenoxypropionic acid, m.p. 76°–78°.

EXAMPLE 15

A mixture of 35.8 g. of the ethyl ester of 2-methyl-2-[p-(1-hydroxy-3-phenoxypropyl)-phenoxy]-propionic acid [obtainable by reacting the ethyl ester of 2-methyl-2-phenoxyproionic acid with 3-chloropropionyl chloride in the presence of $AlCl_3$, reacting the thus-produced ethyl ester of 2-methyl-2-p-(3-chloropropionyl)-phenoxypropionic acid with Na phenolate, and reducing the obtained ethyl ester of 2-methyl-2-p-(3-phenoxypropionyl)-phenoxypropionic acid with $NaBH_4$] and 200 ml. of 48% hydrobromic acid is refluxed for 3 hours under agitation. The mixture is then cooled, extracted with ethyl acetate, and the usual working up operation yields the ethyl ester of 2-methyl-2-p-(4-chromanyl)-phenoxypropionic acid.

EXAMPLE 16

A mixtue of 4.21 g. of the ethyl ester of 2-methyl-2-p-(1-o-hydroxyphenyl-3-bromopropyl)-phenoxypropionic acid [obtainable by reacting 2,4'-dihydroxybenzophenone with malonic acid, decarboxylation to 3-o-hydroxyphenyl-3-p-hydroxyphenylacrylic acid, reduction with $LiAlH_4$ to the alcohol, hydrogenation to 3-o-hydroxyphenyl-3-p-hydroxyphenylpropanol, reaction with the ethyl ester of 2-bromoisobutyric acid to the ethyl ester of 2-methyl-2-p-(1-o-hydroxyphenyl-3-hydroxypropyl)-phenoxypropionic acid, and reaction with $PBr_3$], 0.7 g. of sodium ethylate, and 100 ml. of absolute ethanol is refluxed for 10 hours, then evaporated and worked up with ethyl acetate and water, thus obtaining the ethyl ester of 2-methyl-2-p-(4-chromanyl)-phenoxypropionic acid.

EXAMPLE 17

2 g. of α-phenyl-α-4-(1-methyl-1,2,3,4-tetrahydro-4-quinolyl)-phenoxyacetonitrile (obtainable from 4-(1-methyl-1,2,3,4-tetrahydro-4-quinolyl)-phenol and α-bromo-α-phenylacetonitrile) is refluxed with 2 g. of KOH in 20 ml. of ethanol and 2 ml. of water for 40 hours. The mixture is evaporated, combined with water, extracted with ether, hydrochloric acid is added to pH 5, and the product thus obtained is α-phenyl-α-4-(1-methyl-1,2,3,4-tetrahydro-4-quinolyl)-phenoxyacetic acid; diisopropylamine salt, m.p. 165°–168°.

EXAMPLE 18

10 g. of α-p-chlorophenyl-α-4-(1,2,3,4-tetrahydroquinolino)-phenoxyacetonitrile is refluxed with 60 ml. of acetic acid in 60 ml. of concentrated hydrochloric acid for 2 hours under nitrogen. The mixture is then evaporated, dissolved in dilute NaOH, extracted with ether, hydrochloric acid is added to pH 5, and the product thus obtained is α-p-chlorophenyl-α-4-(1,2,3,4-tetrahydroquinolino)-phenoxyacetic acid; diisopropylamine salt, m.p. 155°–158°.

EXAMPLE 19

3 g. of α-phenyl-α-4-(1-methyl-1,2,3,4-tetrahydro-4-quinolyl)-phenoxyacetamide (obtainable from 4-(1-methyl-1,2,3,4-tetrahydro-4-quinolyl)-phenol and α-bromophenylacetamide) and 5 g. of KOH are refluxed in 100 ml. of ethanol for 3 hours under nitrogen. The mixture is then evaporated, mixed with water, extracted with ether, hydrochloric acid is added to pH 4, and the thus-obtained product is α-phenyl-α-4-(1-methyl-1,2,3,4-tetrahydro-4-quinolyl)-phenoxyacetic acid; diisopropylamine salt, m.p. 165°–168°.

EXAMPLE 20

10 g. of α-p-chlorophenyl-α-4-(1,2,3,4-tetrahydroquinolino)-phenoxyacetyl chloride (obtainable from the acid and $SOCl_2$) is heated with 100 ml. of absolute n-propanol for 3 hours to 95°. The mixture is then evaporated, the residue combined with dilute sodium hydroxide solution, and the aqueous solution extracted with ether. The ether solution is washed twice with dilute NaOH and twice with water, dried, evaporated to remove the ether, and the n-propyl ester of δ-p- chlorophenyl-α-4-(1,2,3,4-tetrahydroquinolino)-phenoxyacetic acid is thus obtained.

EXAMPLE 21

9 g. of α-p-chlorophenyl-α-4-(1,2,3,4-tetrahydroquinolino)-phenoxyacetyl chloride is dissolved in 100 ml. of absolute tetrahydrofuran and mixed with 3 g. of potassium tert.-butylate. The mixture is stirred for 30 minutes at room temperature, filtered, the filtrate evaporated, and the product worked up as described in Example 14, thus producing the tert.-butyl ester of α-p-chloro-phenyl-α-4-(1,2,3,4-tetrahydroquinolino)-phenoxyacetic acid.

EXAMPLE 22

Under agitation, a solution of 18.15 g. of N-chloro-1,2,3,4-tetrahydro-4-quinolone in 30 ml. of concentrated sulfuric acid is added dropwise within 10 minutes to a mixture of 26.25 g. of α-p-chlorophenyl-α-phenoxyacetic acid, 14 g. of iron(II) sulfate heptahydrate, 15 ml. of concentrated sulfuric acid, and 6 ml. of water. The mixture is stirred for another 15 minutes at 20°, then poured onto ice water, washed with ether, sodium hydroxide solution is added to pH 5, and the mixture is extracted with chloroform. From the extract, after evaporation, α-p-chlorophenyl-α-p-(4-oxo-1,2,3,4-tetrahydroquinolino)-phenxoxyacetic acid is obtained, m.p. 180°-185°.

EXAMPLE 23

14.7 g. of 1,2,3,4-tetrahydro-4-quinolone and 3.9 g. of NaNH$_2$ are agitated for one hour at 100° under a nitrogen atmosphere. Then, 38.65 g. of the disodium salt of α-p-chlorophenyl-α-p-sulfophenoxyacetic acid is added thereto (obtainable by the sulfonation of α-p-chlorophenyl-α-phenoxyacetic acid) together with another 15 g. of 1,2,3,4-tetrahydro-4-quinolone, and the mixture is heated for 12 hours under agitation to 120°. After cooling, the mixture is combined with water, washed with ether, and the aqueous phase is adjusted to pH 5, thus producing α-p-chlorophenyl-α-p-(4-oxo-1,2,3,4-tetrahydroquinolino)-phenoxyacetidc acid, m.p. 180°-185°.

EXAMPLE 24

A mixture of 31.4 g. of α-p-chlorophenyl-α-p-aminophenoxyacetic acid hydrochloride, 14.7 g. of 1,2,3,4-tetrahydro-4-quinolone, and 1 g. of AlCl$_3$ is heated in an autoclave for 48 hours to 200°. After cooling and working up the mixture as usual, α-p-chlorophenyl-α-p-(4-oxo-1,2,3,4-tetrahydroquinolino)-phenoxyacetic acid is obtained, m.p. 180°-185°.

EXAMPLE 25

A mixture of 15 g. of 4-chromanol, 20.8 g. of the ethyl ester of 2-methyl-2-phenoxypropionic acid, and 13.4 g. of AlCl$_3$ in 200 ml. of chlorobenzene is agitated overnight at 25°. Then, the mixture is poured on ice water, the organic phase is washed with NaHCO$_3$ solution and with water, the solvent is distilled off, the mixture dissolved in benzene and filtered over Al$_2$O$_3$, thus obtaining the ethyl ester of 2-methyl-2-p-(4-chromanyl)-phenoxypropionic acid.

EXAMPLE 26

A solution of 2 g. of 2-methyl-2-p-(3-chromen-4-yl)-phenoxypropionic acid [obtainable by reacting 4-chromanone with p-(2-carboxy-2-propoxy)-phenylmagnesium bromide in tetrahydrofuran and subsequently working up the product with HCl] in 50 ml. of dioxane is hydrogenated on 0.2 g. of 5% palladium-charcoal until the hydrogen absorption has ceased. The reaction product is filtered, evaporated, and the thus-obtained product is 2-methyl-2-p-(4-chromanyl)-phenoxypropionic acid; cyclohexylamine salt, m.p. 196°-198°.

EXAMPLE 27

A mixture of 0.78 g. of NaNH$_2$ and 3.76 g. of 2-phenyl-2-p-(4-thiochromanyl)-phenoxyacetic acid in 30 ml. of THF is gradually heated to 70° under agitation, then cooled to 20°, 20 ml. of HMPA is added thereto, the mixture cooled to 0°, and, at 0°, 1.5 g. of methyl iodide is added dropwise thereto. Thereafter, the mixture is heated for 3 hours under agitation to 70°, evaporated and worked up as usual, thus obtaining 2-phenyl-2-p-(4-thiochromanyl)-phenoxypropionic acid; Na salt, m.p. 200°-202°.

EXAMPLE 28

At −40°, 50 mg. of iron(III) nitrate is dissolved in 100 ml. of liquid ammonia and then 2.3 g. of Na is likewise dissolved therein under agitation. After 2 hours of stirring, 3.41 g. of 2-phenyl-2-p-(4-chromanyl)-phenoxyacetonitrile is added thereto, the mixture is stirred for 30 minutes, and then 19.2 ml. of dimethyl sulfate is added dropwise within 1 hour. The mixture is further agitated at −35° overnight and then mixed dropwise with another 10 ml. of dimethyl sulfate. After the ammonia has evaporated, the residue is combined with water and extracted with ether. The crude 2-phenyl-2-p-(4-chromanyl)-phenoxypropionitrile obtained after evaporation of the ether is refluxed for 40 hours with 3 g. of KOH in 30 ml. of ethanol and 3 ml. of water. The mixture is then concentrated by evaporation, mixed with water, extracted with ether, and hydrochloric acid is added to pH 5, thus obtaining 2-phenyl-2-p-(4-chromanyl)-phenoxypropionic acid; cyclohexylamine salt, m.p. 190°-193°.

The following examples relate to pharmaceutical preparations containing the effective agents of general Formula I and/or the physiologically acceptable salts thereof:

EXAMPLE A — TABLETS

A mixture consisting of 100 kg. of α-p-chlorophenyl-α-p-(4-oxo-1,2,3,4-tetrahydroquinolino)-phenoxyacetic acid, 400 kg. of lactose, 120 kg. of potato starch, 20 kg. of talc, and 10 kg. of magnesium stearate is pressed to tablets in the usual manner, so that each tablet contains 100 mg. of the effective agent.

EXAMPLE B — DRAGEES

Analogously to Example A, tablets are pressed which are thereafter covered with a coating consisting of sugar, corn starch, talc, and tragacanth.

Analogously, tablets and dragees can be obtained which contain one or more of the remaining effective agents of Formula I and/or the physiologically acceptable salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and

What is claimed is:

1. A compound of the formula

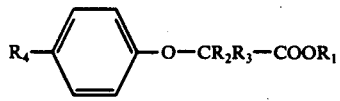

wherein $R_1$ is H or alkyl of 1-4 carbon atoms, $R_2$ is H or alkyl of 1-4 carbon atoms, $R_3$ is methyl, phenyl or chlorophenyl and $R_4$ is 4-chromanyl or 4-thiochromanyl, or a physiologically acceptable salt thereof.

2. A compound of claim 1 wherein $R_4$ is 4-thiochromanyl.

3. A compound of claim 1 wherein $R_4$ is 4-chromanyl.

4. A compound of claim 1 wherein $R_1$ is H, $CH_3$ or $C_2H_5$ and $R_2$ is H or $CH_3$.

5. A compound of claim 1 wherein $R_3$ is $CH_3$, phenyl, m-chlorophenyl or p-chlorophenyl.

6. A compound of claim 1, 2-methyl-2-p-(4-chromanyl)-phenoxypropionic acid, α-phenyl-α-p-(chromanyl)-phenoxyacetic acid, 2-phenyl-2-p-(4-chromanyl)-phenoxypropionic acid, 2-phenyl-2-p-(4-chromanyl)-phenoxypropionic acid ethyl ester, 2-methyl-2-p-(4-thiochromanyl)-phenoxypropionic acid, α-phenyl-α-p-(4-thiochromanyl)-phenoxyacetic acid, 2-phenyl-2-p-(4-thiochromanyl)-phenoxypropionic acid or 2-phenyl-2-p-(4-thiochromanyl)-phenoxypropionic acid ethyl ester.

7. A pharmaceutical composition comprising in unit dosage form a cholesterol blood-level lowering amount of at least one compound of claim 1 in admixture with a pharmaceutically acceptable carrier.

8. A method for lowering the cholesterol blood levels in mammalian patients having abnormally high cholesterol levels which comprises administering to the patient doses of a compound of claim 1 effective to significantly lower cholesterol level of the patient.

* * * * *